United States Patent
Dreyfuss

(10) Patent No.: US 10,076,322 B1
(45) Date of Patent: Sep. 18, 2018

(54) TISSUE BUTTON

(71) Applicant: Arthrex, Inc., Naples, FL (US)

(72) Inventor: Peter J. Dreyfuss, Naples, FL (US)

(73) Assignee: Arthrex, Inc., Naples, FL (US)

( * ) Notice: Subject to any disclaimer, the term of this patent is extended or adjusted under 35 U.S.C. 154(b) by 0 days.

(21) Appl. No.: 15/868,340

(22) Filed: Jan. 11, 2018

(51) Int. Cl.
*A61B 17/04* (2006.01)
*F16G 11/09* (2006.01)
*F16G 11/10* (2006.01)

(52) U.S. Cl.
CPC .. *A61B 17/0401* (2013.01); *A61B 2017/0404* (2013.01); *A61B 2017/0414* (2013.01); *A61B 2017/0448* (2013.01); *A61B 2017/0451* (2013.01); *F16G 11/09* (2013.01); *F16G 11/106* (2013.01)

(58) Field of Classification Search
CPC ............ A61B 17/0401; A61B 17/1327; A61B 2017/0448; A61B 2017/0451; A61B 2017/0454; A61B 2017/045; F16G 11/12; F16G 11/09; F16G 11/10; F16G 11/04; F16G 11/106
USPC .............. 606/232; 24/132 R, 134 R, 134 KB
See application file for complete search history.

(56) References Cited

U.S. PATENT DOCUMENTS

| | | | |
|---|---|---|---|
| 5,702,397 A | 12/1997 | Goble et al. | |
| 5,730,747 A | 3/1998 | Ek et al. | |
| 6,066,160 A | 5/2000 | Colvin et al. | |
| 6,505,384 B1 * | 1/2003 | Renton | B63B 21/04 |
| | | | 114/218 |
| 6,986,781 B2 | 1/2006 | Smith | |
| 7,572,265 B2 | 8/2009 | Stone et al. | |
| 7,585,305 B2 | 9/2009 | Dreyfuss | |
| 7,727,256 B2 | 6/2010 | McGregor | |
| 7,938,847 B2 | 5/2011 | Fanton et al. | |
| 8,118,835 B2 | 2/2012 | Weisel et al. | |
| 8,652,173 B2 | 2/2014 | Mansmann | |
| 8,663,250 B2 | 3/2014 | Weber | |
| 9,307,979 B1 | 4/2016 | Bennett et al. | |
| 9,445,805 B2 | 9/2016 | Snell et al. | |
| 9,463,010 B2 | 10/2016 | Gittings et al. | |
| 9,706,985 B2 | 7/2017 | Allen | |
| 2002/0004668 A1 * | 1/2002 | Bartlett | A61B 17/0401 |
| | | | 606/232 |
| 2005/0241117 A1 * | 11/2005 | Skyba | F16G 11/106 |
| | | | 24/134 R |
| 2006/0282083 A1 * | 12/2006 | Fanton | A61B 17/0401 |
| | | | 606/232 |
| 2010/0292733 A1 * | 11/2010 | Hendricksen | A61B 17/0401 |
| | | | 606/232 |
| 2014/0135834 A1 | 5/2014 | Mansmann | |
| 2014/0296880 A1 | 10/2014 | Heneveld | |

(Continued)

OTHER PUBLICATIONS

Smith & Nephew, Truepass Suture Passer Brochure.

*Primary Examiner* — Diane Yabut
(74) *Attorney, Agent, or Firm* — Carlson, Gaskey & Old, P.C.

(57) ABSTRACT

A tissue button includes a body, a door, and a cross-pin that secures the door to the body. The door pivots relative to the body between an open position and a closed position. A first portion of a suture can be pulled when the door is in the open position, and a second portion of the suture cannot be pulled when the door is in the closed position. A cross-section of the cross-pin taken perpendicular to a longitudinal axis is non-circular.

19 Claims, 6 Drawing Sheets

(56) References Cited

U.S. PATENT DOCUMENTS

2016/0310132 A1 10/2016 Meislin et al.
2017/0042533 A1 2/2017 Lunn et al.

\* cited by examiner

TISSUE BUTTON

BACKGROUND

This disclosure relates to tissue buttons.

SUMMARY

A tissue button secures soft tissue to bone. The tissue button is positioned in a hole in a bone. The tissue button includes a mechanism that allows a portion of a suture to be pulled, but prevents another portion of the suture from being pulled.

Embodiments of a tissue button disclosed herein include a body, a door and a cross-pin. The door is secured to the body by the cross-pin. The door can pivot relative to the body between an open position and a closed position. A suture is looped around the door and includes a first portion and a second portion that extend from the tissue button. The first portion of the suture can be pulled when the door is in the open position. When the first portion of the suture is not being pulled, the flexed cross-pin can provide a spring force to bias the door to the closed position. When the door is in the closed position, the second portion of the suture cannot be pulled. The cross-pin has a longitudinal axis, and a cross-section of the cross-pin taken perpendicular to the longitudinal axis is non-circular.

In an embodiment, a tissue button includes a body and a door that pivots relative to the body between an open position and a closed position. A first portion of a suture can be pulled when the door is in the open position, and an opposing second portion of the suture cannot be pulled when the door is in the closed position. The tissue button includes a cross-pin having a longitudinal axis that secures the door to the body. A cross-section of the cross-pin taken perpendicular to the longitudinal axis is non-circular.

In another embodiment, a tissue button includes a body including opposing walls each including a hole, and a body passage is defined between the opposing walls. A portion of the body passage is partially defined by an end wall that includes a plurality of teeth. The tissue button includes a door that pivots relative to the body between an open position and a closed position. A portion of the door is raised relative to the body in the open position to define a space between the door and the body, and the space receives a suture. A first portion of the suture can be pulled through the space when the door is in the open position. The door is received in the body passage and includes a door passage. The tissue button includes a cross-pin received in the door passage of the door and each of the holes of the body, and the door includes a plurality of teeth. The cross-pin has a longitudinal axis that secures the door to the body. A cross-section of the cross-pin taken perpendicular to the longitudinal axis is non-circular. The cross-pin flexes to move the portion of the door into the body passage of the body to the closed position such that plurality of teeth of the door engage the plurality of teeth of the wall of the body to secure the suture. An opposing second portion of the suture cannot be pulled when the door is in the closed position. The cross-pin comprises Nitinol.

In another embodiment, a method of installing a tissue button includes inserting a tissue button in a hole in a bone and pulling a first portion of a suture relative to the tissue button by pivoting a door of the tissue button relative to a body of the tissue button to an open position. A cross-pin that secures the door to the body flexes when in the open position, and the cross-pin has a non-circular cross-section taken perpendicular to a longitudinal axis of the cross-pin. The method also includes using a spring force to pivot the door to a closed position to prevent a second portion of the suture from being pulled through the tissue button.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein.

DETAILED DESCRIPTION

Figure 1:
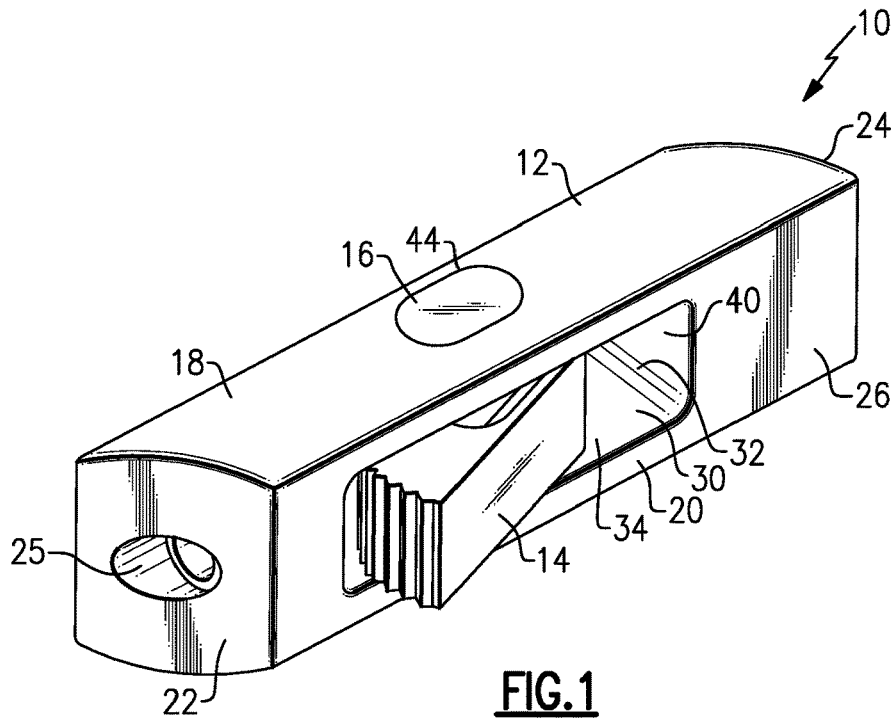
FIG. 1 is a schematic perspective view of an embodiment of a tissue button in an open position.

A tissue button secures soft tissue to bone. The tissue button is positioned in a hole in a bone. The tissue button includes a mechanism that allows a portion of a suture to be pulled, but prevents another portion of the suture from being pulled.

Embodiments of a tissue button disclosed herein include a body, a door and a cross-pin. The door is secured to the body by the cross-pin. The door can pivot relative to the body between an open position and a closed position. A suture is looped around the door and includes a first portion and a second portion that extend from the tissue button. The first portion of the suture can be pulled when the door is in the open position. When the first portion of the suture is not being pulled, the flexed cross-pin can provide a spring force to bias the door to the closed position. When the door is in the closed position, the second portion of the suture cannot be pulled. The cross-pin has a longitudinal axis, and a cross-section of the cross-pin taken perpendicular to the longitudinal axis is non-circular.

In an embodiment, a tissue button includes a body and a door that pivots relative to the body between an open position and a closed position. A first portion of a suture can be pulled when the door is in the open position, and an opposing second portion of the suture cannot be pulled when the door is in the closed position. The tissue button includes a cross-pin having a longitudinal axis that secures the door to the body. A cross-section of the cross-pin taken perpendicular to the longitudinal axis is non-circular.

In an embodiment, the cross-pin comprises Nitinol. In an embodiment, the body and the door comprise titanium. In an embodiment, the body of the tissue button includes a passage to receive a surgical instrument. In an embodiment, the body includes opposing walls each including a hole, a body passage is defined between the opposing walls, the door is received in the body passage and includes a door passage, and the cross-pin is received in the door passage of the door and each of the holes of the opposing walls. In an embodiment, a portion of the body passage is partially defined by an end wall that includes a plurality of teeth. In an embodiment, each of the plurality of teeth are rounded. In an embodiment, the plurality of teeth extend across a width of the end wall. In an embodiment, the door passage of the door includes a central passage and a chamfered surface on opposing sides of the central passage. In an embodiment, the central passage of the door includes two non-parallel walls, a first arced wall connected to each of the non-parallel walls having a first radius, and a second arced wall connected to each of the non-parallel walls having a second radius, and the second radius is greater than the first radius. In an embodiment, the door includes a plurality of teeth proximate to the second arc. In an embodiment, each of the plurality of teeth are rounded. In an embodiment, the plurality of teeth extend across a width of the door. In an embodiment, the body includes a plurality of teeth and the door includes a plurality of teeth, a portion of the door is raised relative to the body in the open position to define a space between the door and the body to receive a suture that can pass through the space, and the cross-pin flexes to move the portion of the door into the body passage of the body when in the closed position such that plurality of teeth of the door engage the plurality of teeth of the wall of the body to secure the suture therebetween.

In another embodiment, a tissue button includes a body including opposing walls each including a hole, and a body passage is defined between the opposing walls. A portion of the body passage is partially defined by an end wall that includes a plurality of teeth. The tissue button includes a door that pivots relative to the body between an open position and a closed position. A portion of the door is raised relative to the body in the open position to define a space between the door and the body, and the space receives a suture. A first portion of the suture can be pulled through the space when the door is in the open position. The door is received in the body passage and includes a door passage. The tissue button includes a cross-pin received in the door passage of the door and each of the holes of the body, and the door includes a plurality of teeth. The cross-pin has a longitudinal axis that secures the door to the body. A cross-section of the cross-pin taken perpendicular to the longitudinal axis is non-circular. The cross-pin flexes to move the portion of the door into the body passage of the body to the closed position such that plurality of teeth of the door engage the plurality of teeth of the wall of the body to secure the suture. An opposing second portion of the suture cannot be pulled when the door is in the closed position. The cross-pin comprises Nitinol.

In an embodiment, each of the plurality of teeth are rounded and extend across a width of the end wall, and each of the plurality of teeth are rounded and extend across a width of the door. In an embodiment, the door passage includes a central passage and a chamfered surface on opposing sides of the central passage, the central passage of the door includes two non-parallel walls, a first arced wall connected to each of the non-parallel walls having a first radius, and a second arced wall connected to each of the non-parallel walls having a second radius, and the second radius is greater than the first radius.

In another embodiment, a method of installing a tissue button includes inserting a tissue button in a hole in a bone and pulling a first portion of a suture relative to the tissue button by pivoting a door of the tissue button relative to a body of the tissue button to an open position. A cross-pin that secures the door to the body flexes when in the open position, and the cross-pin has a non-circular cross-section taken perpendicular to a longitudinal axis of the cross-pin. The method also includes using a spring force to pivot the door to a closed position to prevent a second portion of the suture from being pulled through the tissue button.

Figure 2:
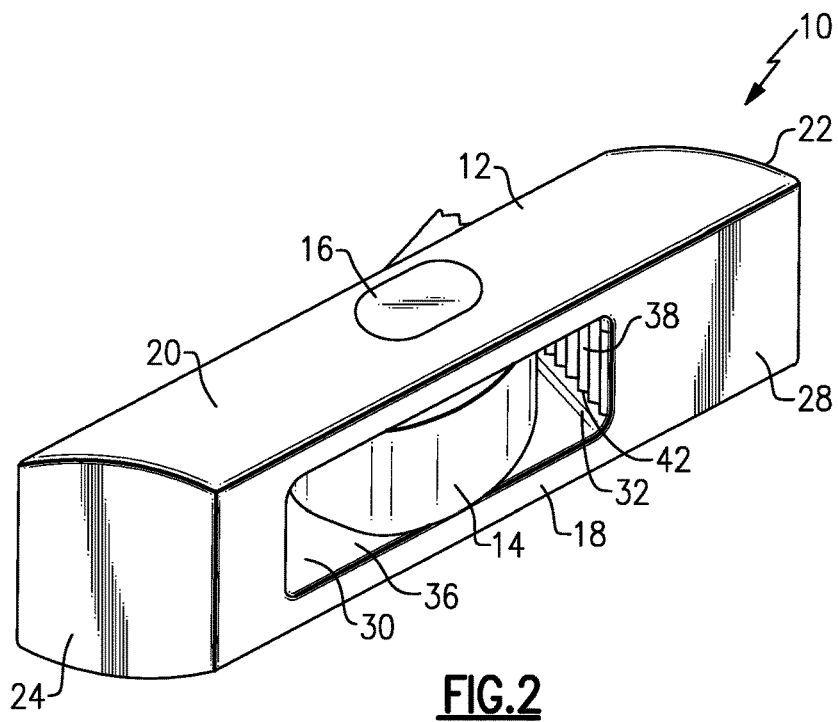
FIG. 2 is another schematic perspective view of the tissue button of FIG. 1.
Figure 3:
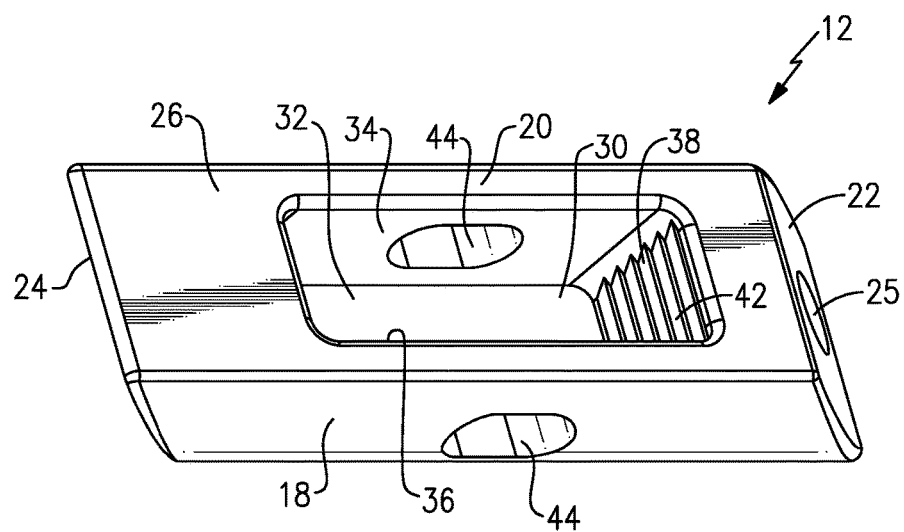
FIG. 3 is a schematic perspective view of an embodiment of a body of the tissue button.
Figure 4:
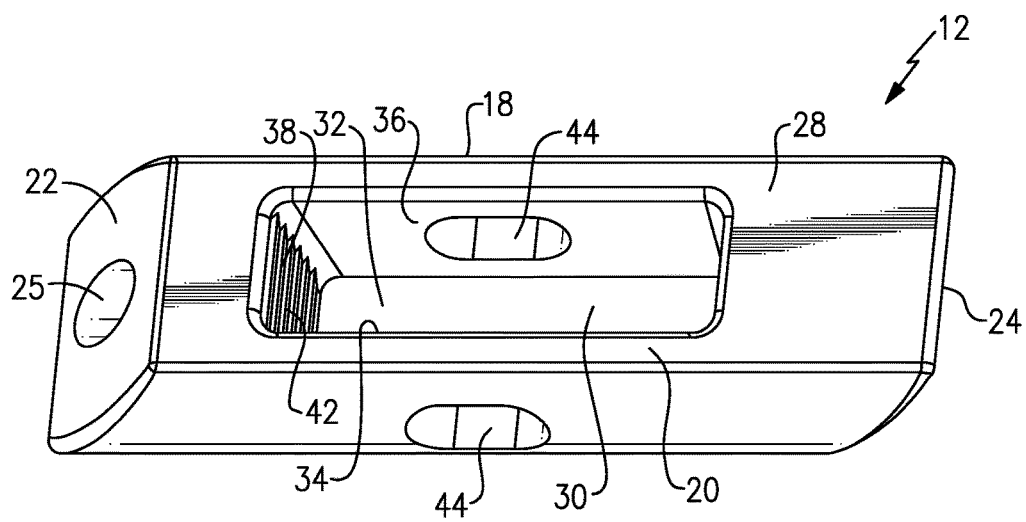
FIG. 4 is another schematic perspective view of the body of the tissue button of FIG. 3.
Figure 5:
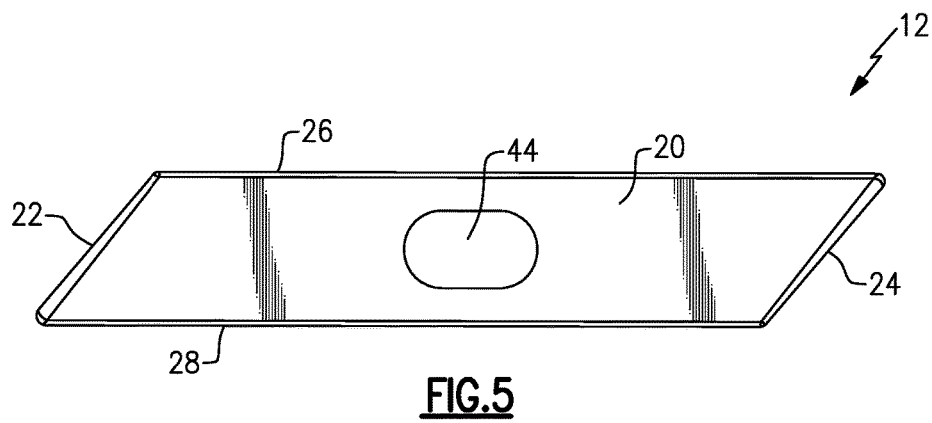
FIG. 5 is a schematic side view of the body of the tissue button of FIG. 3.
Figure 6:
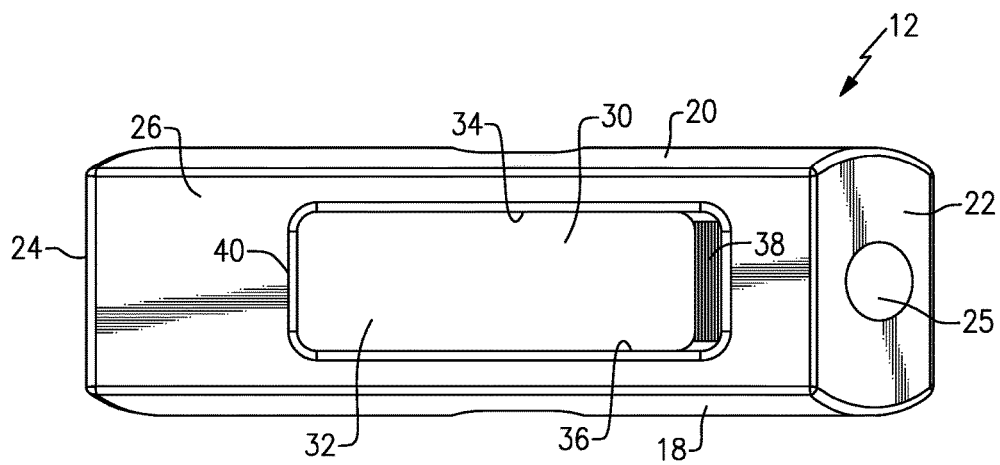
FIG. 6 is a schematic top view of the body of the tissue button of FIG. 3.

FIGS. 1 to 2 illustrate a tissue button 10 in an open position. The tissue button 10 includes a body 12 and a door 14 secured to the body 12 with a cross-pin 16. In one exemplary embodiment, the tissue button 10 is made of titanium. In another exemplary embodiment, the body 12 and the door 14 are made of titanium, and the cross-pin 16 is made of Nitinol. Nitinol is a more flexible metal than titanium, allowing the cross-pin 16 to flex.

FIGS. 3 to 7 illustrate the body 12 of the tissue button 10. The body 12 includes two opposing parallel exterior side walls 18 and 20, two opposing parallel exterior end walls 22 and 24, and two opposing parallel exterior opening walls 26 and 28. The exterior side walls 18 and 20 and the exterior opening walls 26 and 28 are substantially perpendicular to each other. The exterior end walls 22 and 24 are non-perpendicular to the exterior opening walls 26 and 28. In one exemplary embodiment, the edge where the walls meet adjacent walls is smooth and rounded.

The exterior end wall 22 includes a passage 25 that can receive a surgical instrument 78. Each of the exterior side walls 18 and 20 includes a hole 44. Each of the exterior opening walls 26 and 28 include an opening 30. A body passage 32 is defined between the walls 18, 20, 22, 24, 26 and 28, and the openings 30 are located at each end of the body passage 32.

Figure 7:
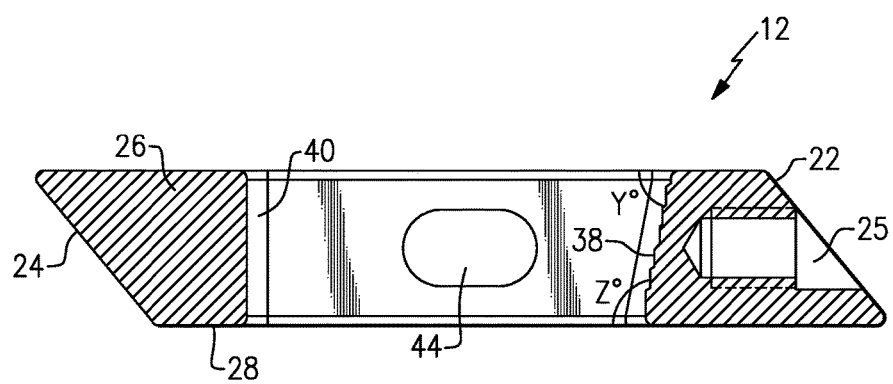
FIG. 7 is a schematic cross-sectional side view of the body of the tissue button of FIG. 3.

The body passage 32 is defined by two interior side walls 34 and 36 and two interior end walls 38 and 40. The interior side walls 34 and 36 are substantially parallel to each other. The interior end wall 40 is perpendicular to the interior side walls 34 and 36. The interior side wall 38 intersects the exterior opening wall 28 at an obtuse angle (Z° as shown in FIG. 7) and intersects the exterior opening wall 26 at an acute angle (Y° as shown in FIG. 7). The wall 40 includes a plurality of teeth 42. In one exemplary embodiment, the plurality of teeth 42 are each rounded to prevent suture fraying. In one exemplary embodiment, the plurality of teeth 42 extend across a width of the wall 40.

Figure 10:
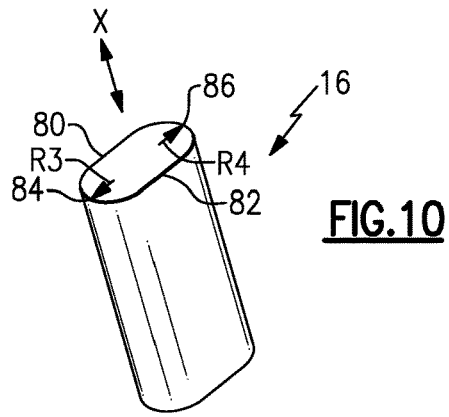
FIG. 10 is a schematic perspective view of an embodiment of a cross-pin of the tissue button.

A cross-pin 16 (shown further in FIG. 10) secures the door 14 to the exterior side walls 18 and 20 of the body 12. In one exemplary embodiment, the cross-pin 16 extends along a longitudinal axis X. In one exemplary embodiment, the cross-pin 16 has a non-circular cross-section taken perpendicular to the longitudinal axis X. In one exemplary embodiment, the cross-section of the cross-pin 16 includes two parallel walls 80 and 82, a first arched wall 84 having a radius R3, and a second arched wall 86 having a radius R4. The radii R3 and R4 are substantially equal. In one exemplary embodiment, the cross-pin 16 is oval.

In one exemplary embodiment, the cross-pin 16 is received in both of the holes 44 in the exterior side walls 18 and 20. In one exemplary embodiment, the cross-pin 16 is press-fit in the holes 44 and flush with an exterior surface of the body 12.

Figure 8:
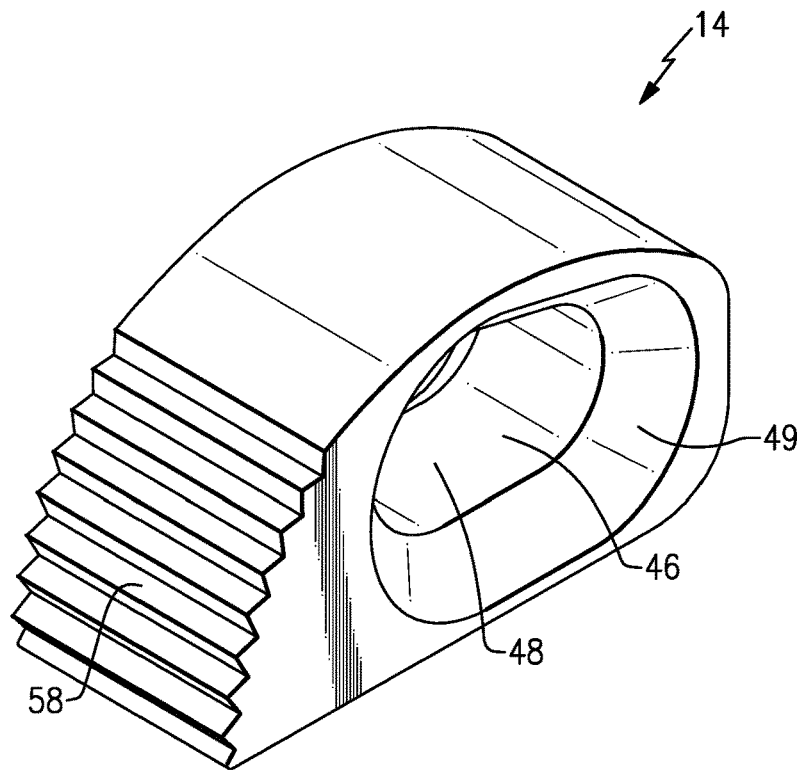
FIG. 8 is a schematic perspective view of an embodiment of a door of the tissue button.
Figure 9:
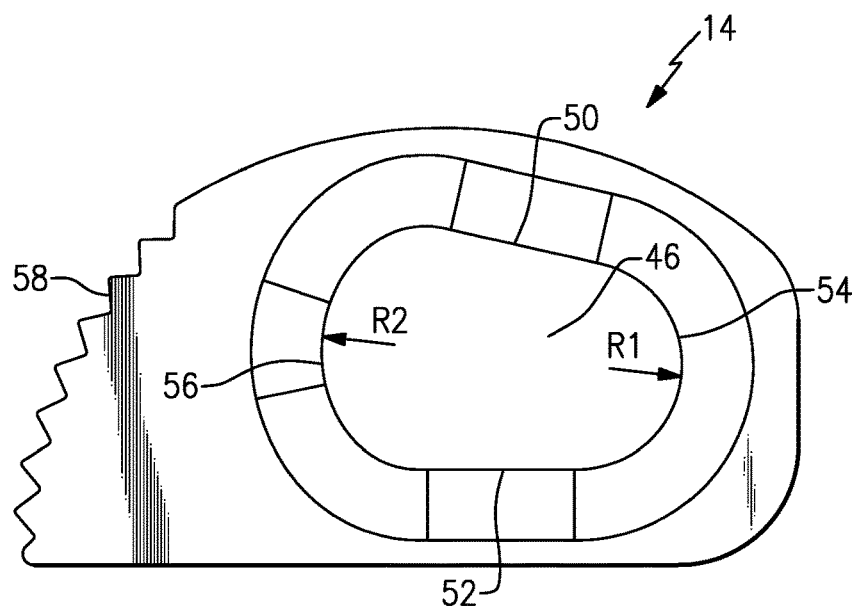
FIG. 9 is a schematic cross-sectional side view of the door of the tissue button of FIG. 8.

As shown in FIGS. 8 and 9, the door 14 is received in the body passage 32 of the body 12 and can pivot relative to the body 12 between an open position and a closed position. The door 14 includes a door passage 46, and the cross-pin 16 extends through the door passage 46 of the door 14 and is received in the holes 44 of the body 12 to secure the door 14 to the body 12. In one exemplary embodiment, the door passage 46 includes a central passage 48 and a chamfered surface 49 on opposing sides of the central passage 48. In one exemplary embodiment, the central passage 48 includes two non-parallel walls 50 and 52, a first arced wall 54 connected to each of the non-parallel walls 50 and 52 having a radius R1, and a second arced wall 56 connected to each of the non-parallel walls 50 and 52 having a radius R2. The radius R2 is greater than the radius R1. Also, the radius R2 is greater than radii R3 and R4. When the cross-pin 16 is received in the door passage 46, the larger radius R2 allow the door 14 to pivot about the cross-pin 16.

In one exemplary embodiment, the door 14 also includes a plurality of teeth 58 on the exterior wall closest to the second arc 56 that can engage the plurality of teeth 42 of the wall 40 of the body 12. In one exemplary embodiment, the plurality of teeth 58 are each rounded. In one exemplary embodiment, the plurality of teeth 58 extend across a width of the door 14.

Figure 11:
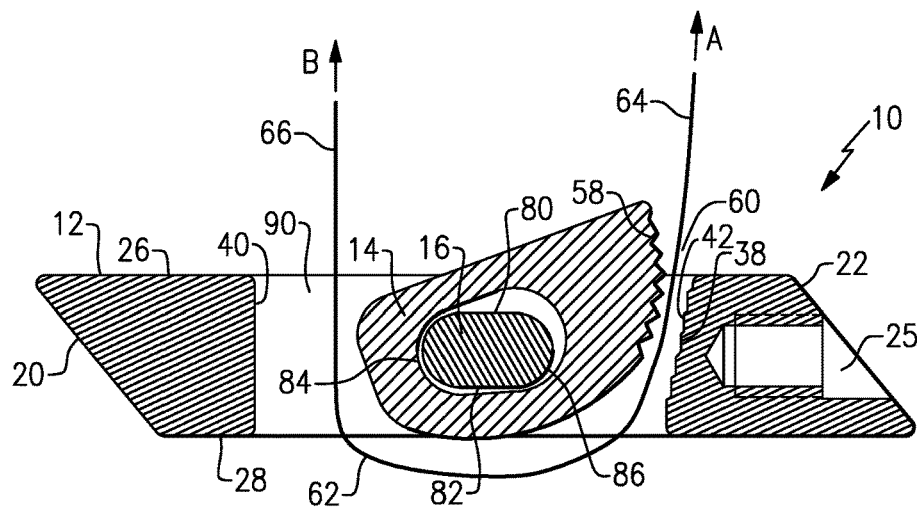
FIG. 11 is a schematic cross-sectional side view of an embodiment of the tissue button in an open position.

FIG. 11 shows the tissue button 10 in an open position. The teeth 58 of the door 14 are spaced from the teeth 42 of the wall 38, defining a space 60 therebetween. In the open position, the door 14 is raised relative to the body 12. In one exemplary embodiment, the door 14 is raised relative to the exterior opening wall 26. A suture 62 is located around the door 14 such that a portion 64 of the suture 62 is received in the space 60, and another portion 66 of the suture 62 is received in another space 90 on an opposing side of the door 14.

Figure 12:
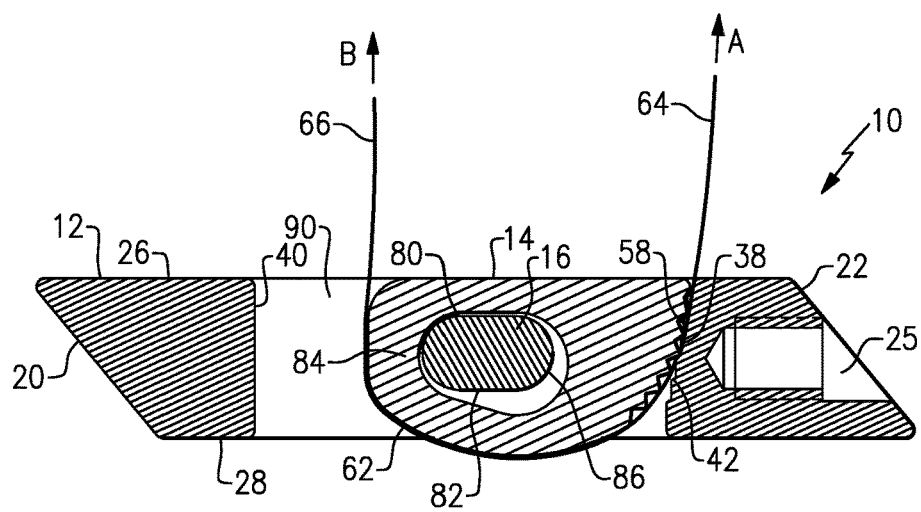
FIG. 12 is a schematic cross-sectional side view the tissue button of FIG. 11 in a closed position.

In the open position, the space 60 allows the portion 64 of the suture 62 to be pulled freely through the tissue button 10 in a direction A. When the portion 64 of the suture 62 is pulled in the direction A, the cross-pin 12 engages a surface of the hole 44, and the cross-pin 12 slightly flexes, further allowing the suture 62 through the space 60. When the portion 64 of the suture 62 is no longer pulled, the flexed cross-pin 12 provides a spring return force to pivot the door 14 about the cross-pin 16 and close the door 14 as shown in FIG. 12, locking the suture 62 in place. In the closed position, the door 14 is located in the body passage 32 of the body 12. In one exemplary embodiment, the door 14 is flush with the exterior opening wall 26.

When door 14 is in the closed position, and the portion 66 of the suture 62 is pulled in the direction B, the suture 62 is trapped between the door 14 that is closed and the wall 40. The teeth 42 and 58 also retain the suture 62 to prevent the suture 62 from being pulled through the tissue button 10 in the direction B. The rounded plurality of teeth 42 and 58 that trap the suture 62 help to prevent the suture 62 from fraying when the tissue button 10 and the door are in the closed position.

If the portion 64 of the suture 62 is then pulled in the direction A, the door 14 pivots away from the body 12 to the open position, allowing the suture 62 to be pulled in the direction A.

Figure 13:
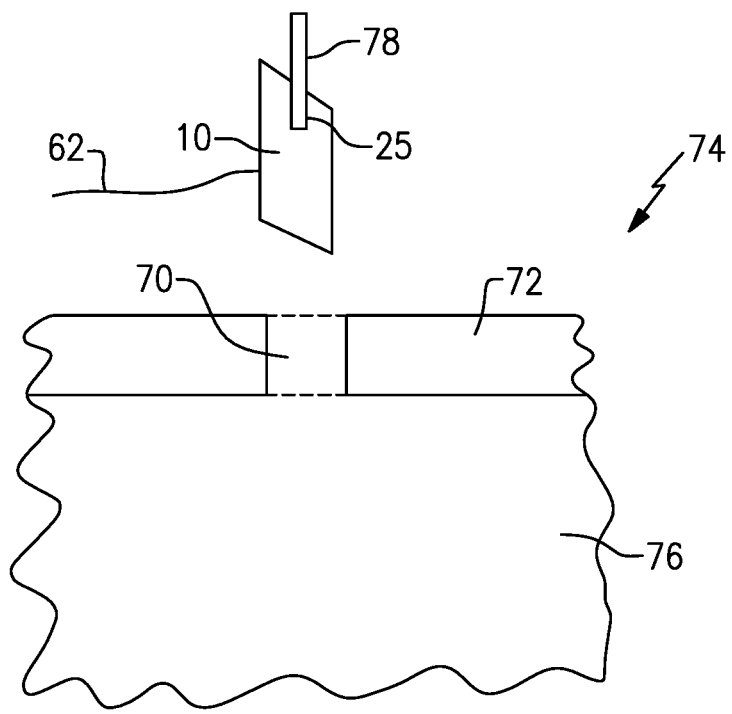
FIG. 13 is a schematic view of an embodiment of a tissue button being inserted in a bone.
Figure 14:
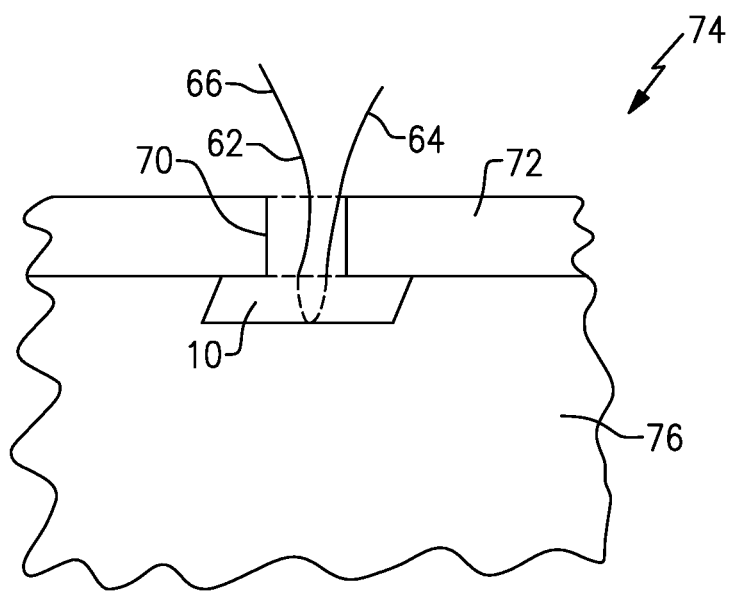
FIG. 14 is a schematic view of the tissue button of FIG. 13 installed in a bone.

As shown in FIG. 13, a hole 70 is drilled through cortical bone 72 of a bone 74. The suture 62 is looped around the door 14 (shown in FIGS. 11 and 12) and passes through the spaces 60 and 90. A surgical instrument 78, such as an inserter, is received in the passage 25 of the tissue button 10 and is used to push the tissue button 10 through the hole 70 and into cancellous tissue 76 of the bone 74. Once in the cancellous tissue 76, the locked portion 66 of the suture 62 can be pulled to position the tissue button 10 in the desired position, as shown in FIG. 14.

While the tissue button 10 is located in the cancellous tissue 76 and the tissue button 10 is in the open position, the suture 62 can be pulled in the direction A to lengthen the portion 64 of the suture 62. If the portion 66 of the suture 62 is pulled in the direction B, the door 14 pivots to the closed position, locking the suture 62 and preventing the suture 62 from being pulled in the direction B.

The tissue button 10 can be used to repair biceps (proximal and distal) and during pectoral tenodesis surgeries. The tissue button 10 can also be used with anterior cruciate ligament repair, knee cruciate repair, medial and lateral ligament repair, elbow ligament reconstruction, ankle ligament and tendon repair, and any other procedures.

The foregoing description is only exemplary of the principles of the invention. Many modifications and variations are possible in light of the above teachings. It is, therefore, to be understood that within the scope of the appended claims, the invention may be practiced otherwise than using the example embodiments which have been specifically described. For that reason the following claims should be studied to determine the true scope and content of this invention.

What is claimed is:

1. A tissue button comprising:
   a body;
   a door that pivots relative to the body between an open position and a closed position, wherein a first portion of a suture can be pulled when the door is in the open position, and an opposing second portion of the suture cannot be pulled when the door is in the closed position, wherein the door includes a door passage, the door passage includes two non-parallel walls, a first arced wall connected to each of the non-parallel walls having a first radius, a second arced wall connected to each of the non-parallel walls having a second radius, and the second radius is greater than the first radius; and
   a cross-pin having a longitudinal axis that secures the door to the body, wherein a cross-section of the cross-pin taken perpendicular to the longitudinal axis is non-circular.

2. The tissue button as recited in claim 1 wherein the cross-pin comprises Nitinol.

3. The tissue button as recited in claim 1 wherein the body and the door comprise titanium.

4. The tissue button as recited in claim 1 wherein the body of the tissue button includes a passage to receive a surgical instrument.

5. The tissue button as recited in claim 1 wherein the body includes opposing walls each including a hole, and a body passage is defined between the opposing walls, wherein the door is received in the body passage, and the cross-pin is received in the door passage of the door and each of the holes of the opposing walls.

6. The tissue button as recited in claim 5 wherein a portion of the body passage is partially defined by an end wall that includes a plurality of teeth.

7. The tissue button as recited in claim 6 wherein each of the plurality of teeth are rounded.

8. The tissue button as recited in claim 6 wherein the plurality of teeth extend across a width of the end wall.

9. The tissue button as recited in claim 5 wherein the door passage of the door includes a central passage and a chamfered surface on opposing sides of the central passage.

10. The tissue button as recited in claim 1 wherein the body includes a plurality of teeth and the door includes a plurality of teeth, a portion of the door is raised relative to the body in the open position to define a space between the door and the body to receive a suture that can pass through the space, and the cross-pin flexes to move the portion of the door into the body passage of the body when in the closed position such that plurality of teeth of the door engage the plurality of teeth of the wall of the body to secure the suture therebetween.

11. The tissue button as recited in claim 1 wherein the body has a longitudinal axis and a body passage, and a portion of a suture located inside the body passage is substantially perpendicular to the longitudinal axis of the body.

12. A tissue button comprising:
a body, wherein the body includes opposing walls each including a hole, and a body passage is defined between the opposing walls;
a door that pivots relative to the body between an open position and a closed position, wherein a first portion of a suture can be pulled when the door is in the open position, and an opposing second portion of the suture cannot be pulled when the door is in the closed position, wherein the door is received in the body passage and includes a door passage, wherein the door passage of the door includes a central passage and a chamfered surface on opposing sides of the central passage, wherein the central passage of the door includes two non-parallel walls, a first arced wall connected to each of the non-parallel walls having a first radius, and a second arced wall connected to each of the non-parallel walls having a second radius, and the second radius is greater than the first radius; and
a cross-pin having a longitudinal axis that secures the door to the body, wherein a cross-section of the cross-pin taken perpendicular to the longitudinal axis is non-circular, and the cross-pin is received in the door passage of the door and each of the holes of the opposing walls.

13. The tissue button as recited in claim 12 wherein the door includes a plurality of teeth proximate to the second arc.

14. The tissue button as recited in claim 13 wherein each of the plurality of teeth are rounded.

15. The tissue button as recited in claim 13 wherein the plurality of teeth extend across a width of the door.

16. A tissue button comprising:
a body including opposing walls each including a hole, and a body passage is defined between the opposing walls, wherein a portion of the body passage is partially defined by an end wall that includes a plurality of teeth;
a door that pivots relative to the body between an open position and a closed position, wherein a portion of the door is raised relative to the body in the open position to define a space between the door and the body, and the space receives a suture, a first portion of the suture can be pulled through the space when the door is in the open position, the door is received in the body passage and includes a door passage, a cross-pin is received in the door passage of the door and each of the holes of the body, and the door includes a plurality of teeth, wherein the door includes a door passage, the door passage includes two non-parallel walls, a first arced wall connected to each of the non-parallel walls having a first radius, a second arced wall connected to each of the non-parallel walls having a second radius, and the second radius is greater than the first radius,
the cross-pin having a longitudinal axis that secures the door to the body, wherein a cross-section of the cross-pin taken perpendicular to the longitudinal axis is non-circular, the cross-pin flexes to move the portion of the door into the body passage of the body to the closed position such that plurality of teeth of the door engage the plurality of teeth of the wall of the body to secure the suture, and an opposing second portion of the suture cannot be pulled when the door is in the closed position, wherein the cross-pin comprises Nitinol.

17. The tissue button as recited in claim 16 wherein each of the plurality of teeth are rounded and extend across a width of the end wall, and each of the plurality of teeth are rounded and extend across a width of the door.

18. A tissue button comprising:
a body including opposing walls each including a hole, and a body passage is defined between the opposing walls, wherein a portion of the body passage is partially defined by an end wall that includes a plurality of teeth;
a door that pivots relative to the body between an open position and a closed position, wherein a portion of the door is raised relative to the body in the open position to define a space between the door and the body, and the space receives a suture, a first portion of the suture can be pulled through the space when the door is in the open position, the door is received in the body passage and includes a door passage, a cross-pin is received in the door passage of the door and each of the holes of the body, and the door includes a plurality of teeth, wherein the door passage includes a central passage and a chamfered surface on opposing sides of the central passage, the central passage of the door includes two non-parallel walls, a first arced wall connected to each of the non-parallel walls having a first radius, and a second arced wall connected to each of the non-parallel walls having a second radius, and the second radius is greater than the first radius; and
the cross-pin having a longitudinal axis that secures the door to the body, wherein a cross-section of the cross-pin taken perpendicular to the longitudinal axis is non-circular, the cross-pin flexes to move the portion of the door into the body passage of the body to the closed position such that plurality of teeth of the door engage the plurality of teeth of the wall of the body to secure the suture, and an opposing second portion of the suture cannot be pulled when the door is in the closed position, wherein the cross-pin comprises Nitinol.

19. A method of installing a tissue button comprising:
inserting a tissue button in a hole in a bone;
pulling a first portion of a suture relative to the tissue button by pivoting a door of the tissue button relative to a body of the tissue button to an open position, wherein the door includes a door passage, the door passage includes two non-parallel walls, a first arced wall connected to each of the non-parallel walls having a first radius, a second arced wall connected to each of the non-parallel walls having a second radius, and the second radius is greater than the first radius, wherein a cross-pin that secures the door to the body flexes when in the open position, and the cross-pin has a non-circular cross-section taken perpendicular to a longitudinal axis of the cross-pin; and using a spring force to pivot the door to a closed position to prevent a second portion of the suture from being pulled through the tissue button.

* * * * *

UNITED STATES PATENT AND TRADEMARK OFFICE
CERTIFICATE OF CORRECTION

PATENT NO. : 10,076,322 B1  
APPLICATION NO. : 15/868340  
DATED : September 18, 2018  
INVENTOR(S) : Peter J. Dreyfuss Page 1 of 1

It is certified that error appears in the above-identified patent and that said Letters Patent is hereby corrected as shown below:

In the Claims

In Claim 11, Column 7, Line 20; after "portion of" replace "a" with --the--

In Claim 16, Column 8, Line 14; after "such that" insert --the--

In Claim 18, Column 8, Line 51; after "such that" insert --the--

Signed and Sealed this  
Nineteenth Day of November, 2019

Andrei Iancu  
*Director of the United States Patent and Trademark Office*